(12) United States Patent
Larson et al.

(10) Patent No.: US 8,302,610 B1
(45) Date of Patent: Nov. 6, 2012

(54) SPINE IMMOBILIZER WITH REMOVABLE STRAPS

(76) Inventors: Donald O. Larson, Audubon, MN (US); Kasey P. Larson, Detroit Lakes, MN (US)

(*) Notice: Subject to any disclaimer, the term of this patent is extended or adjusted under 35 U.S.C. 154(b) by 417 days.

(21) Appl. No.: 12/623,905

(22) Filed: Nov. 23, 2009

(51) Int. Cl.
*A61F 5/37* (2006.01)
(52) U.S. Cl. .................. 128/870; 128/876; 5/630; 5/636
(58) Field of Classification Search .......... 128/869–870, 128/874, 876; 5/630, 636, 638, 640; 24/33 A, 24/33 R, 71 T, 163 R, 310, 578.13, 590.1, 24/591.1, 595.1, 651, 652, 658, 302, 305, 24/307, 312, 314, 317, 318, 344, 374, DIG. 51, 24/572.1, 578.15, 579.09, 580.1, 598.1, 265 BC
See application file for complete search history.

(56) References Cited

U.S. PATENT DOCUMENTS

| | | | |
|---|---|---|---|
| 1,767,451 A * | 6/1930 | Hedge | 152/241 |
| 3,406,433 A * | 10/1968 | Frey | 24/647 |
| 4,034,748 A * | 7/1977 | Winner | 602/19 |
| 4,151,842 A | 5/1979 | Miller | |
| 4,589,407 A | 5/1986 | Koledin et al. | |
| 4,601,075 A * | 7/1986 | Smith | 5/628 |
| 4,776,327 A | 10/1988 | Russell | |
| 4,779,858 A | 10/1988 | Saussereau | |
| 4,899,736 A | 2/1990 | Nesbitt | |
| 4,918,753 A * | 4/1990 | Mermillod | 2/10 |
| 4,979,520 A | 12/1990 | Boone, Jr. et al. | |
| 5,014,374 A | 5/1991 | Williams | |
| 5,027,833 A | 7/1991 | Calkin | |
| 5,058,575 A | 10/1991 | Anderson | |
| 5,121,756 A | 6/1992 | Koledin | |
| 6,341,383 B1 * | 1/2002 | Beltrani | 2/452 |

* cited by examiner

*Primary Examiner* — Loan Thanh
*Assistant Examiner* — Camtu Nguyen
(74) *Attorney, Agent, or Firm* — Neustel Law Offices

(57) ABSTRACT

A spine immobilizer with removable straps for efficiently providing removable straps upon a spine immobilizer for cleaning, maintenance, replacement, or inspection purposes. The spine immobilizer generally includes an immobilizer panel comprised of a semi-rigid structure, wherein the immobilizer panel has a central support, first wings laterally extending from a first end of the central support, and second wings laterally extending from a second end of the central support, a plurality of connectors extending from a back side of the immobilization panel along the first wings and the second wings, and a plurality of strap assemblies removably connected to the plurality of connectors. The plurality of strap assemblies are adapted to removably connect to a correlating strap assembly via a buckle-connector structure and join the first wings and join the second wings of the immobilization panel about a patient.

9 Claims, 7 Drawing Sheets

SPINE IMMOBILIZER WITH REMOVABLE STRAPS

CROSS REFERENCE TO RELATED APPLICATIONS

Not applicable to this application.

STATEMENT REGARDING FEDERALLY SPONSORED RESEARCH OR DEVELOPMENT

Not applicable to this application.

BACKGROUND OF THE INVENTION

1. Field of the Invention

The present invention relates generally to a spine immobilizer and more specifically it relates to a spine immobilizer with removable straps for efficiently providing removable straps upon a spine immobilizer for cleaning, maintenance, replacement, or inspection purposes.

2. Description of the Related Art

Any discussion of the related art throughout the specification should in no way be considered as an admission that such related art is widely known or forms part of common general knowledge in the field.

Spine immobilizers, such as the Kendrick Extrication Device (KED) are widely used today in the extraction of persons from damaged motor vehicles, construction sites, and the like, as wells as transportation of persons to medical facilities and other locations in which the immobilization of the head, neck, and spine are necessary. When transporting an individual with a spine immobilizer attached, it can be common for the straps of the spine immobilizer to become soiled in bodily waste, blood, or other fluids from the individual. The straps and fasteners can also become cut or damaged when utilizing the spine immobilizer.

Currently, the straps are generally fixedly sewn or attached to the vest, thus making removal of the straps for maintenance difficult or impossible. The entire spine immobilizer must be replaced or decontaminated which can lead to unnecessary costs, when only maintenance of the straps is needed. Because of the inherent problems with the related art, there is a need for a new and improved spine immobilizer with removable straps for efficiently providing removable straps upon a spine immobilizer for cleaning, maintenance, replacement, or inspection purposes.

BRIEF SUMMARY OF THE INVENTION

A system for efficiently providing removable straps upon a spine immobilizer for cleaning, maintenance, replacement, or inspection purposes. The invention generally relates to a spine immobilizer which includes an immobilizer panel comprised of a semi-rigid structure, wherein the immobilizer panel has a central support, first wings laterally extending from a first end of the central support, and second wings laterally extending from a second end of the central support, a plurality of connectors extending from a back side of the immobilization panel along the first wings and the second wings, and a plurality of strap assemblies removably connected to the plurality of connectors. The plurality of strap assemblies are adapted to removably connect to a correlating strap assembly via a buckle-connector structure and join the first wings and join the second wings of the immobilization panel about a patient.

There has thus been outlined, rather broadly, some of the features of the invention in order that the detailed description thereof may be better understood, and in order that the present contribution to the art may be better appreciated. There are additional features of the invention that will be described hereinafter and that will form the subject matter of the claims appended hereto. In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

A. Overview

Figure 1:
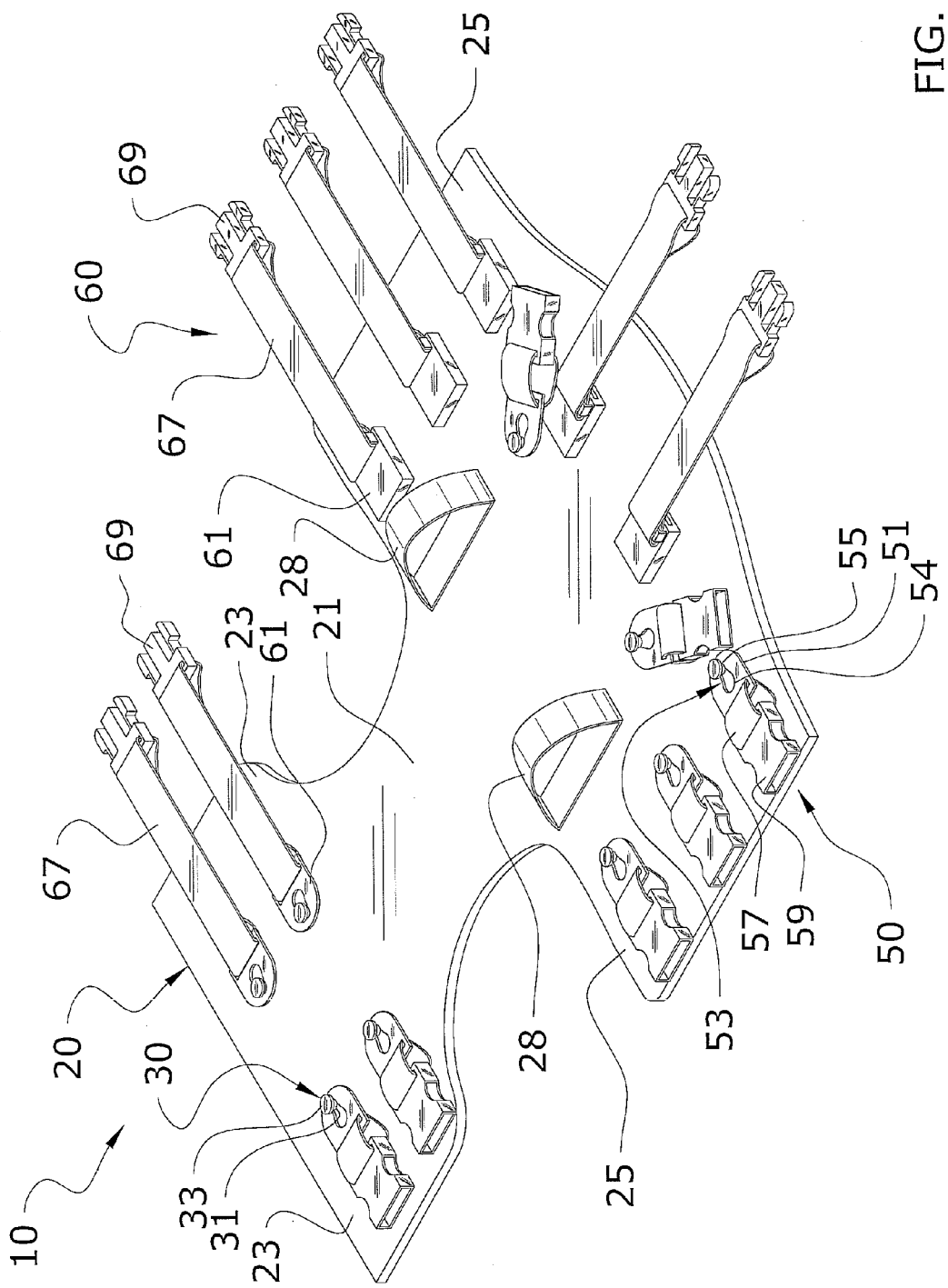
FIG. 1 is an upper perspective view of the present invention with the strap assemblies attached to the connectors.
Figure 2:
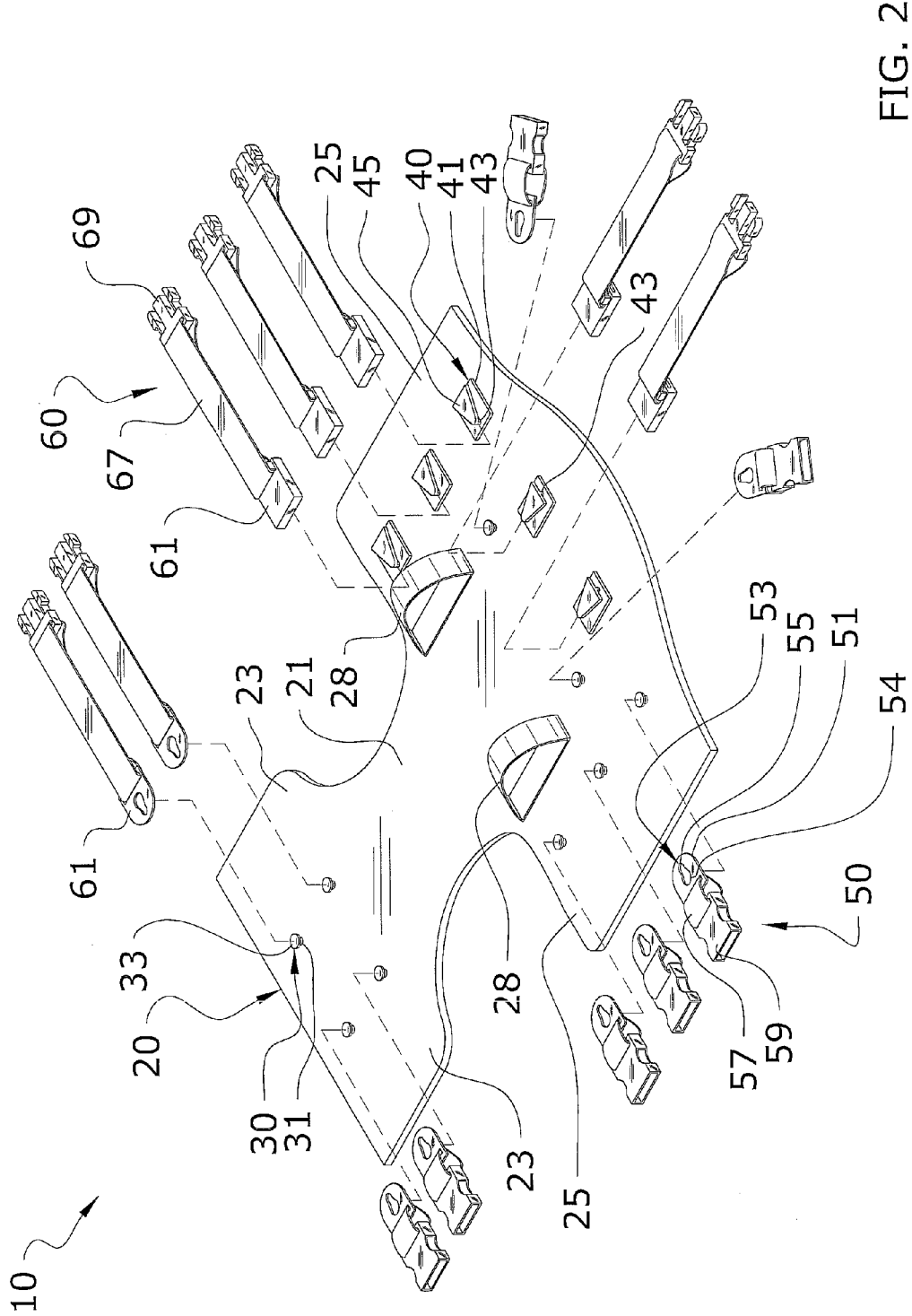
FIG. 2 is an upper perspective view of the present invention with the strap assemblies exploded from the connectors.
Figure 3:
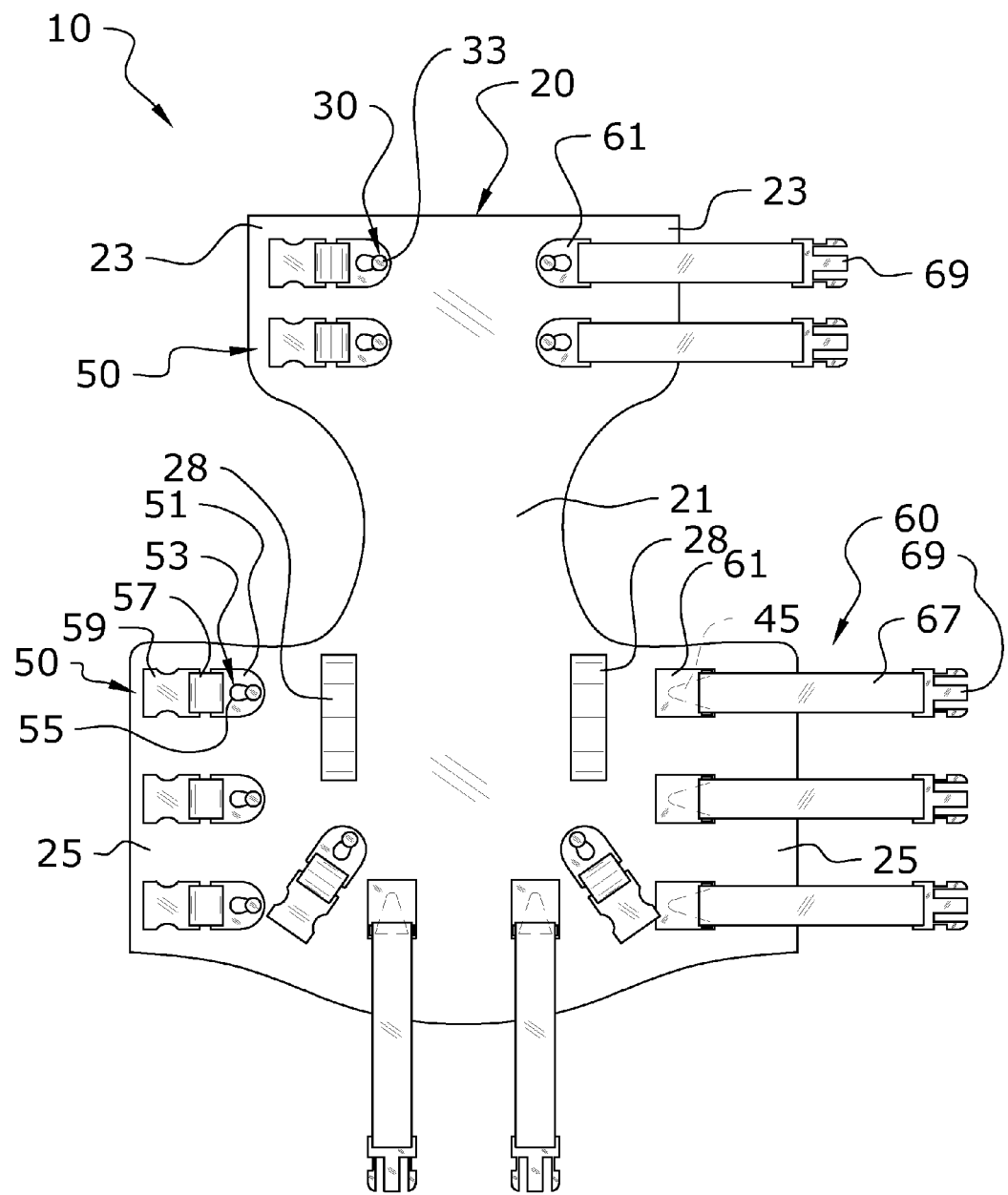
FIG. 3 is a top view of the present invention with the strap assemblies attached to the connectors.
Figure 4:
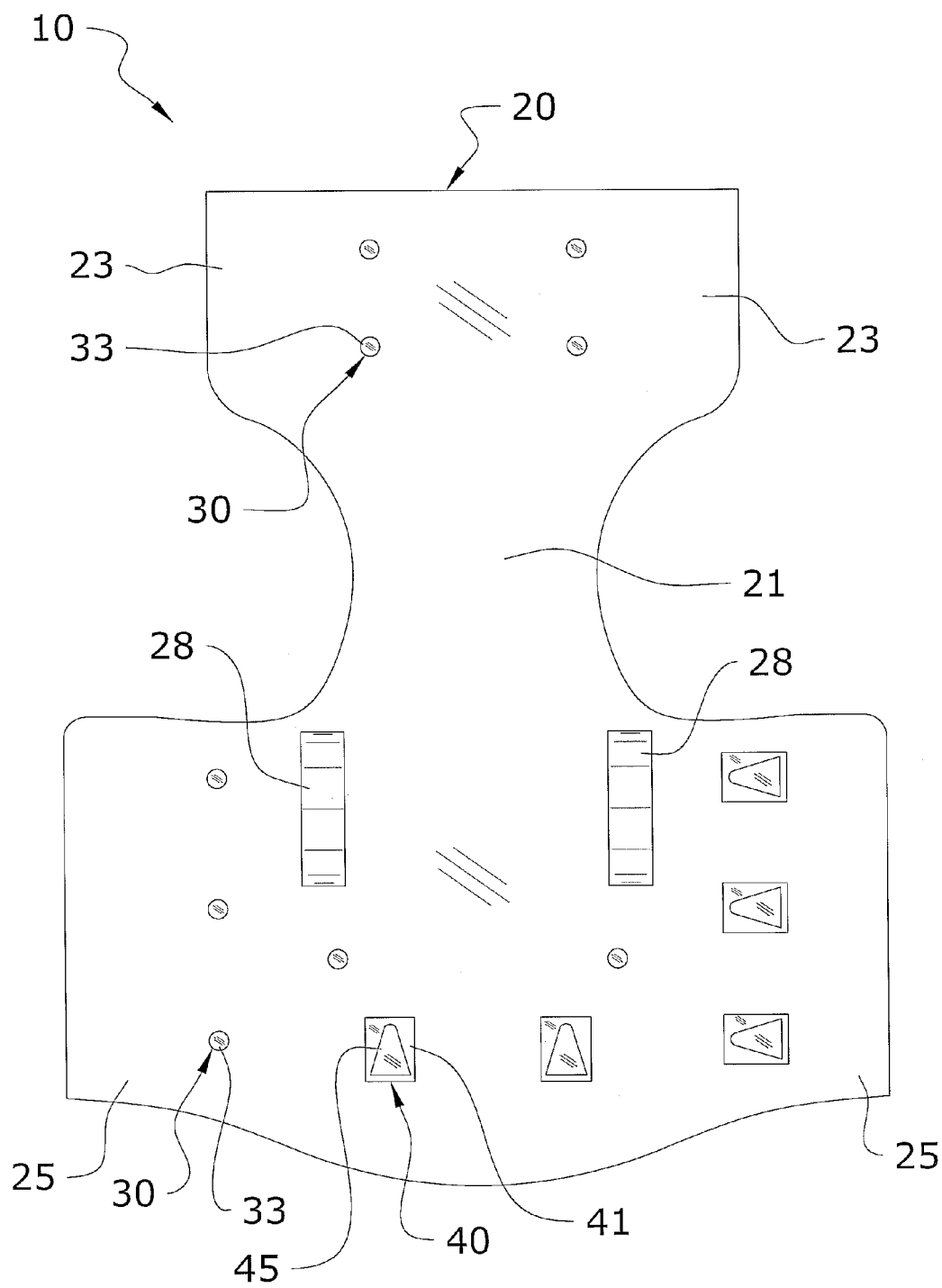
FIG. 4 is a top view of the present invention with the strap assemblies removed from the connectors.

Turning now descriptively to the drawings, in which similar reference characters denote similar elements throughout the several views, FIGS. 1 through 7 illustrate a spine immobilizer with removable straps 10, which comprises an immobilizer panel 20 comprised of a semi-rigid structure, wherein the immobilizer panel 20 has a central support 21, first wings 23 laterally extending from a first end of the central support 21, and second wings 25 laterally extending from a second end of the central support 21, a plurality of connectors 30, 40 extending from a back side of the immobilization panel 20 along the first wings 23 and the second wings 25, and a plurality of strap assemblies 50, 60 removably connected to the plurality of connectors 30, 40. The plurality of strap assemblies 50, 60 are adapted to removably connect to a correlating strap assembly 50, 60 via a buckle-connector structure 59, 69 and join the first wings 23 and join the second wings 25 of the immobilization panel 20 about a patient. The connectors 30, 40 and strap assemblies 50, 60 are positioned along the first wings 23 and second wings 25 of the panel 20 to connect the panel 20 to the upper (head), central (torso), and lower (legs) of the patient.

B. Immobilizer Panel

The panel 20 is used to immobilize a patient's head, neck, and spine by wrapping around the back side of the patient and connecting around the patient via the strap assemblies 50, 60. The panel 20 is comprised of a semi-rigid structure. The panel 20 may include a plurality of rigid support bars longitudinally extending therethrough for providing support and may have a nylon or flexible exterior material for providing flexibility to the panel 20 to wrap around the patient. The panel 20 of the present invention is further preferably comprised of a similar structure to a conventional Kendrick Extraction Device (KED).

The panel 20 includes a central support 21 for extending along the spine and behind the head of the patient. Extending laterally outward from the central support 21 on an upper end for partially wrapping around the head is a set of first wings 23 and extending laterally outward on a lower end for partially wrapping around the torso is a set of second wings 25. The first wings 23 and the second wings 25 are generally integrally formed with the central support 21 to comprise a unitary structure. The panel 20 may also include loop members 28 along a back side of the central support 21 for providing handles to the panel 20.

C. Connectors

The immobilizer panel 20 includes the plurality of first connectors 30 each for removably connecting a first strap assembly 50. The first connectors 30 extend from a back side of the panel 20 (opposite the patient). The immobilizer panel 20 also includes the plurality of second connectors 40 each for removably connecting a second strap assembly 60. The second connectors 40 extend from a back side of the panel 20 (opposite the patient). It is appreciated that a majority of the connectors 30, 40 may be comprised of the first connectors 30, or the second connectors 40, or the number of connectors 30, 40 may be divided equally.

Each first connector 30 mechanically connects to a respective second connector 40 through the connection of the first strap assembly 50 and the second strap assembly 60 extending therefrom. Alternately, for the first wings 23, the first connectors 30 are solely used rather than the use of both first connectors 30 and second connectors 40. The straps 60 thus include correlating receivers 51. In the preferred embodiment, the panel 20 includes three sets of connectors 30, 40 and strap assemblies 50, 60 for the torso of the patient extending from the second wings 25, two sets of connectors 30, 40 and strap assemblies 50, 60 for the legs of the patient extending from the second wings 25, and two sets of connectors 30 and strap assemblies 50, 60 for the head of the patient extending from the first wings 23. It is appreciated that the connectors 30 extending from the head portion or first wing 23 of the panel 20 are both of a similar construction to allow for swiveling of the strap assemblies 50, 60.

The first connectors 30 and the second connectors 40 are preferably used along the second wings 25 of the panel 20 for wrapping around the torso and legs of the patient. The first connectors 30 and the second connectors 40 may also be used along the first wings 23 of the panel 20 for wrapping around the head of the patient and may additionally be used along the central support 21 between the first wings 23 and the second wings 25 if necessitated.

In the preferred embodiment, the first connectors 30 are each comprised of similar structures. The first connectors 30 each include a fixedly attached post 31 extending outwardly from the panel 20 and a terminal flange 33 extending from the post 31. The terminal flange 33 has a diameter greater than the post 31, wherein the post 31 and terminal flange 33 comprise a T-shaped structure for removably receiving the first strap assembly 50 and additionally the second strap assembly 60 in the case of both of the strap assemblies 50, 60 connecting to a T-shaped first connector 30.

In the preferred embodiment, the second connectors 40 are each comprised of similar structures. The second connectors 40 each include a plate 41 fixedly attached to the panel 20, a vertical column 43 extending outwardly therefrom and a raised member 45 laterally extending from the vertical column 43. The raised member 45 projects laterally outward from the column 43 and is preferably comprised of flat arrowhead or triangular-shaped structure for slidably receiving the receiver 61 of the second strap assembly 60. The raised member 45 is offset from the plate 41 and panel 20 via the vertical column 43 thus allowing for a portion of the receiver 61 of the second strap assembly 60 to be sandwiched therebetween.

D. Strap Assemblies

The strap assemblies 50, 60 removably attach to each other through the use of male and female connectors 59, 69 and the panel 20 through the use of the connectors 30, 40 to allow for removal of the strap assemblies 50, 60 for cleaning, maintenance, replacement, etc. of the strap assemblies 50, 60. The strap assemblies 50, 60 may be adjustable in length to accommodate for different sized individuals.

In the preferred embodiment, the first strap assembly 50 includes a plate-like receiver 51 having a closed-ended slot 53 formed therein. The slot 53 includes a first portion 54 having a first diameter and a second portion 55 extending therefrom having a second diameter. The first portion 54 has a greater diameter than the second portion 55. The diameter of the first portion 54 preferably is similar or slightly larger than the diameter of the terminal flange 33 and the diameter of the second portion 55 is slightly larger than the diameter of the post 31 yet less than the diameter of the terminal flange 33 so that the receiver 51 may be slid from the first portion 54 to the second portion 55 upon the first connector 30 to secure the receiver 51 to the first connector 30.

Extending from the receiver 51 is a shortened strap 57 which may be adjustable in length. Extending from the strap 57 is a female connector 59, preferably of a buckle-type connector. The first strap assembly 50 is comprised of a structure to be removably attached to the panel 20 on a first end and removably attached to the second strap assembly 60 on the second end without the use or requirement of tools to allow for quick attaching and detaching in emergency situations.

Figure 5:
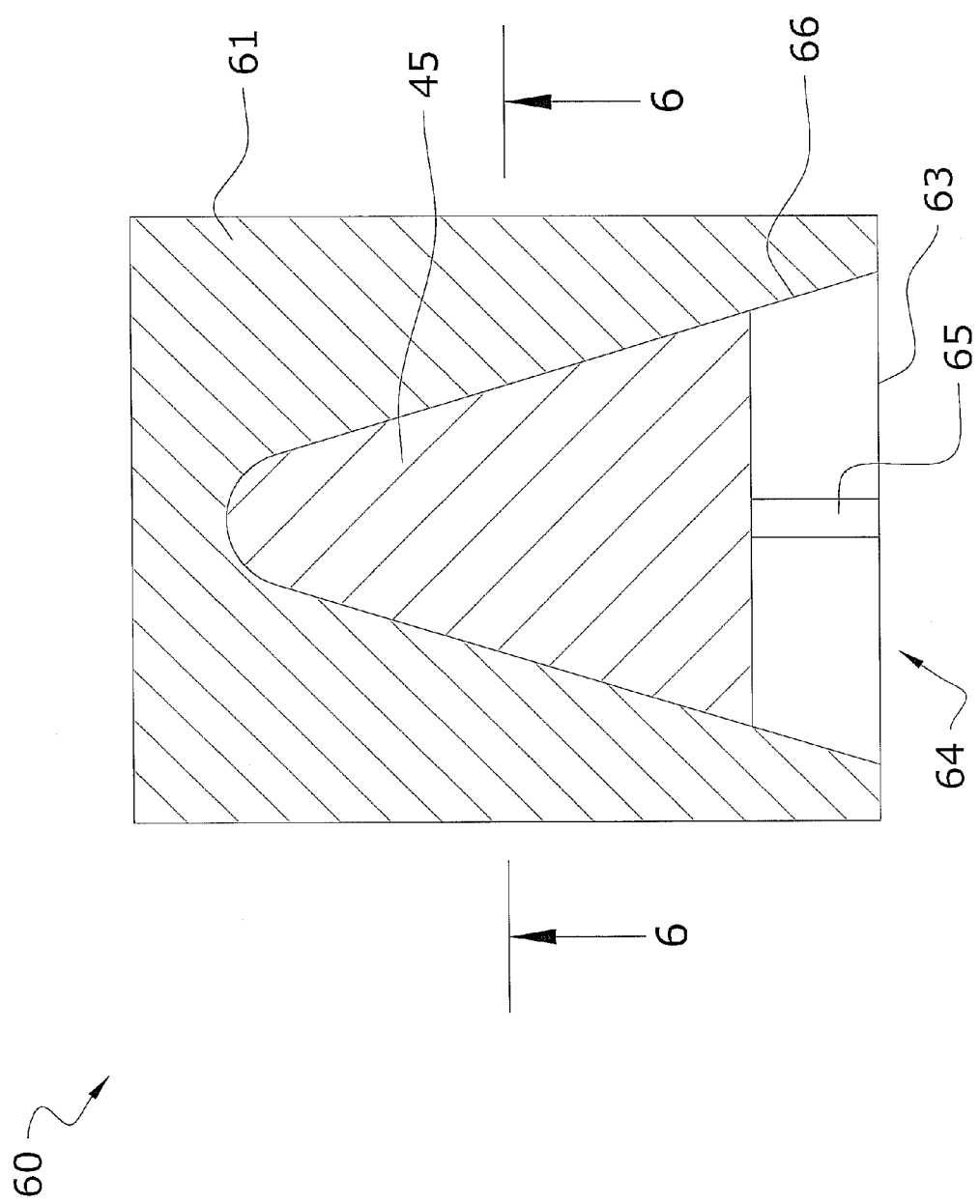
FIG. 5 is a top sectional view of the second connector and correlating receiver.
Figure 6:
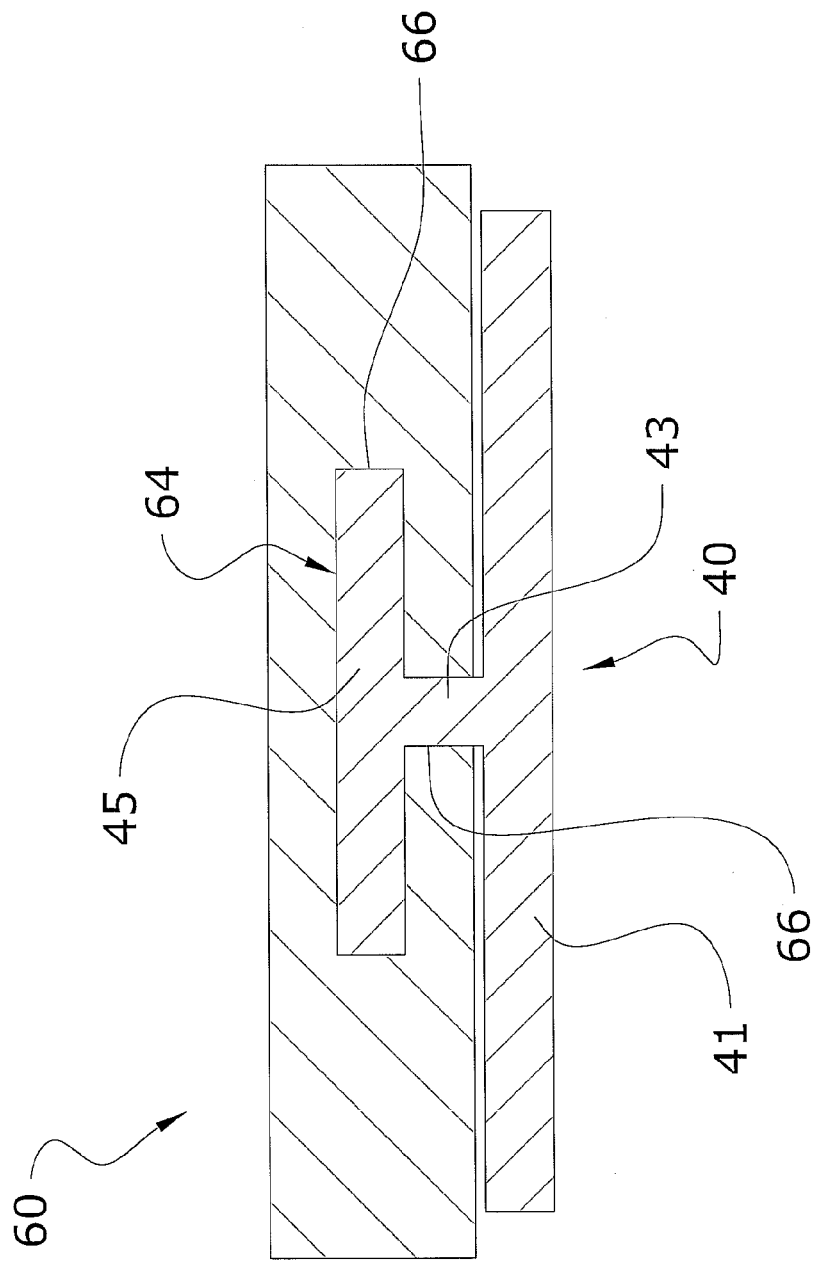
FIG. 6 is a side sectional view taken along lines 6-6 of FIG. 5.
Figure 7:
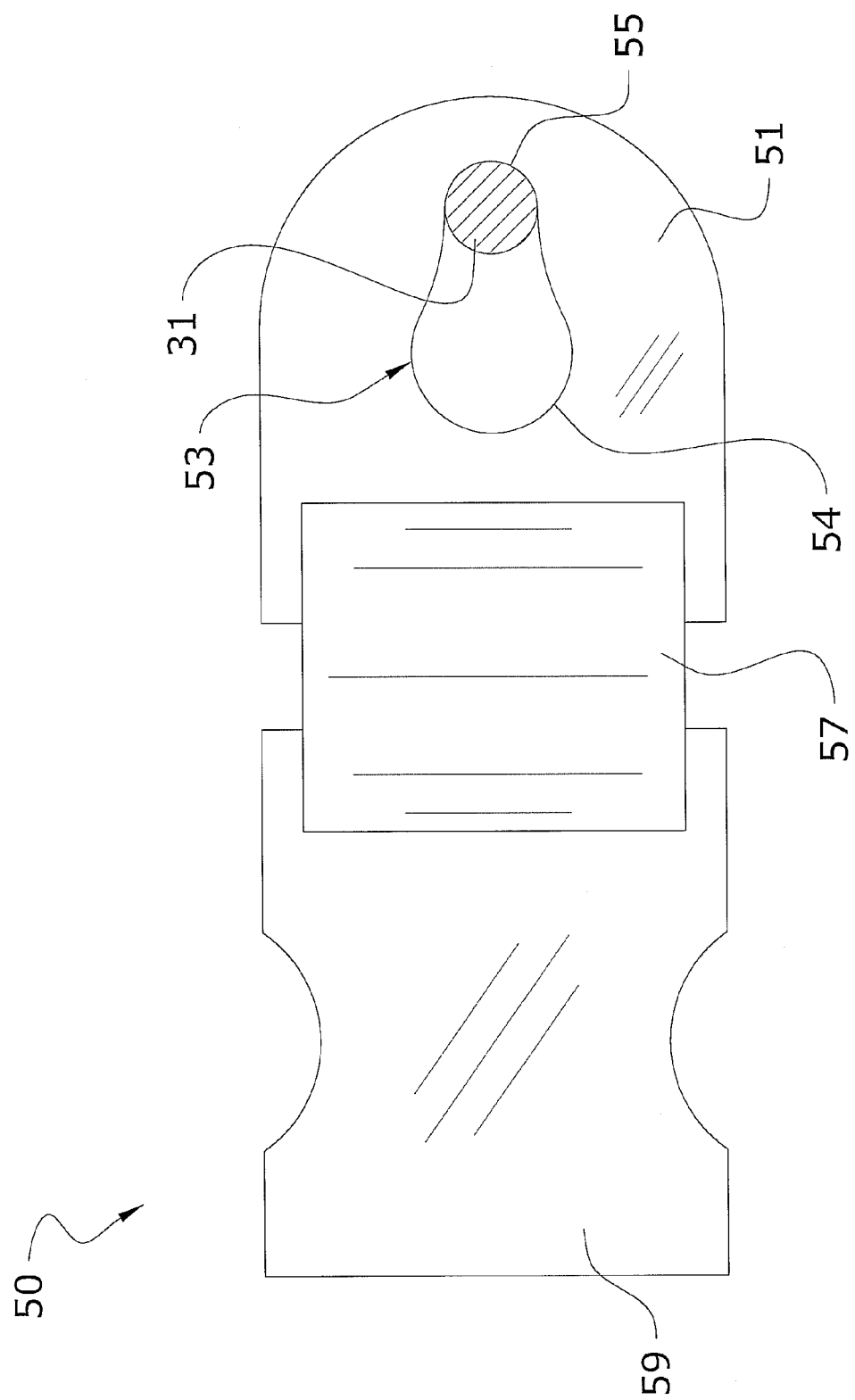
FIG. 7 is a top sectional view of the first connector and correlating receiver.

In the preferred embodiment, the second strap assembly 60 includes a receiver 61 having an open end 63 leading to a slot 64 formed therein. The slot 64 receives the raised member 45 through a second portion 66 of the slot 64 and vertical column 43 through a first portion 65 of the slot 64 through the open end 63, wherein the receiver 61 wraps around the raised member 45 of the second connector 40 to be secured thereon. The slot 64 is thus comprised of a similar cross-sectional shape as the second connector 40, such as a narrowing T-shape structure as illustrated in FIGS. 5 and 6.

Extending from the receiver 61 is a lengthened strap 67 which may be adjustable in length. Extending from the strap 67 is a male connector 69, preferably of a buckle-type connector. The second strap assembly 60 is comprised of a structure to be removably attached to the panel 20 on a first end and removably attached to the first strap assembly 50 on the second end without the use or requirement of tools to allow for quick attaching and detaching in emergency situations.

Generally the strap assemblies 50, 60 extending around the torso and legs of the patient from the second wings 25 of the panel 20 utilize both the first connector 30 on one end and the second connector 40 on an opposing end. However, as stated previously, the strap assemblies 50, 60 extending around the head of the patient from the first wings 23 of the panel 20 preferably only utilize the first connectors 30 to allow for the connected strap assemblies 50, 60 to swivel thus accommodating different height individuals. Thus, the second strap assemblies 60 located at the first wing 23 include the receiver 51 from the first strap assembly 50 to removably connect to the first connector 30 and not the second connector 40. Alternate combinations of connectors 30, 40 and strap assemblies 50, 60 may be appreciated.

E. Operation of Preferred Embodiment

In use, the panel 20 is placed around the back side of a patient with the connectors 30, 40 opposite the patient. A plurality of first strap assemblies 50, 60 are attached to respective first connectors 30 and a plurality of second strap assemblies 50, 60 are attached to respective second connectors 40. The first strap assemblies 50, 60 are then wrapped around the patient and connected to a correlating second strap assembly 60 to secure the panel 20 to the patient and immobilize the spine of the patient.

Unless otherwise defined, all technical and scientific terms used herein have the same meaning as commonly understood by one of ordinary skill in the art to which this invention belongs. Although methods and materials similar to or equivalent to those described herein can be used in the practice or testing of the present invention, suitable methods and materials are described above. All publications, patent applications, patents, and other references mentioned herein are incorporated by reference in their entirety to the extent allowed by applicable law and regulations. In case of conflict, the present specification, including definitions, will control. The present invention may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

The invention claimed is:

1. A spine immobilization device, comprising:
an immobilizer panel comprised of a semi-rigid structure;
wherein said immobilizer panel has a central support, first wings laterally extending from a first end of said central support, and second wings laterally extending from a second end of said central support;
a plurality of connectors extending from a back side of said immobilization panel along said first wings and said second wings; and
a plurality of strap assemblies removably connected to said plurality of connectors;
wherein said plurality of connectors are comprised of a raised-triangular structure, wherein said raised-triangular structure has a T-shape cross-sectional structure;
wherein said plurality of strap assemblies include male and female buckle-structured connectors for connecting to each other;
wherein said plurality of strap assemblies each include a receiver for removably receiving said plurality of connectors;
wherein said receiver includes an open-ended slot for slidably receiving a connector of said plurality of connectors;
wherein said slot has a T-shape cross-sectional structure.

2. A spine immobilization device, comprising:
an immobilizer panel comprised of a semi-rigid structure;
wherein said immobilizer panel has a central support, first wings laterally extending from a first end of said central support, and second wings laterally extending from a second end of said central support;
a plurality of connectors extending from a back side of said immobilization panel along said first wings and said second wings; and
a plurality of strap assemblies removably connected to said plurality of connectors;
wherein said plurality of connectors each include a post extending from said immobilization panel and a terminal flange extending from said post;
wherein said plurality of connectors are comprised of a raised-triangular structure;
wherein said raised-triangular structure has a T-shape cross-sectional structure;
wherein said plurality of strap assemblies each include a receiver for removably receiving said plurality of connectors;
wherein said receiver includes an open-ended slot for slidably receiving a connector of said plurality of connectors;
wherein said slot has a T-shape cross-sectional structure.

3. The spine immobilization device of claim 2, wherein said plurality of strap assemblies include male and female buckle-structured connectors for connecting to each other.

4. The spine immobilization device of claim 2, wherein said terminal flange has a greater diameter than said post.

5. The spine immobilization device of claim 4, wherein said plurality of strap assemblies each include a receiver for removably receiving said plurality of connectors.

6. The spine immobilization device of claim 5, wherein said receiver includes a closed-ended slot having a first portion and a second portion.

7. The spine immobilization device of claim 6, wherein said first portion has a first diameter and wherein said second portion has a second diameter, wherein said first diameter is greater than said second diameter.

8. A spine immobilization device, comprising:
an immobilizer panel comprised of a semi-rigid structure;
wherein said immobilizer panel has a central support, first wings laterally extending from a first end of said central support, and second wings laterally extending from a second end of said central support;
a plurality of connectors extending from a back side of said immobilization panel along said first wings and said second wings; and
a plurality of strap assemblies removably connected to said plurality of connectors;
wherein said plurality of connectors are comprised of a raised-triangular structure, wherein said raised-triangular structure has a T-shape cross-sectional structures;
wherein said plurality of strap assemblies each include a receiver for removably receiving said plurality of connectors;
wherein said receiver includes an open-ended slot for slidably receiving a connector of said plurality of connectors;
wherein said slot has a T-shape cross-sectional structure.

9. The spine immobilization device of claim 8, wherein said plurality of strap assemblies include male and female buckle-structured connectors for connecting to each other.

* * * * *